United States Patent [19]

Nathans et al.

[11] Patent Number: 4,767,709

[45] Date of Patent: Aug. 30, 1988

[54] GROWTH-RELATED HORMONES

[75] Inventors: Daniel Nathans; Daniel I. H. Linzer, both of Baltimore, Md.

[73] Assignee: The Johns Hopkins University, Baltimore, Md.

[21] Appl. No.: 625,499

[22] Filed: Jun. 28, 1984

[51] Int. Cl.$^4$ .......................... C12N 5/00; C12N 1/20; C12N 1/00; C07H 21/00

[52] U.S. Cl. ................................ 435/240.2; 435/172.3; 435/253; 435/320; 536/27; 530/399; 935/13; 935/27; 935/31; 935/32; 935/70

[58] Field of Search .................. 435/6, 68, 172.3, 253, 435/320, 240, 240.2; 536/27; 436/501; 530/399; 935/4, 9, 11, 27, 31, 32, 33, 70, 78, 13, 50

[56] References Cited

U.S. PATENT DOCUMENTS

| | | | |
|---|---|---|---|
| H000,245 | 4/1987 | Bahl | 935/13 X |
| 4,431,739 | 2/1984 | Riggs | 935/73 X |
| 4,446,235 | 5/1984 | Seeburg | 935/29 X |
| 4,564,593 | 1/1986 | Tsukamoto et al. | 935/4 X |

OTHER PUBLICATIONS

D. I. H. Linzer and D. Nathans, Changes in Specific mRNAs Following Serum Stimulation of Cultured Mouse Cells: Increase in a Prolactin-Related mRNA in: Cancer Cells 1, pp. 111-115, 1984.
Miller, W. I. et al., *Endocrine Reviews*, vol. 4; No. 2, 1983, pp. 97-130.
Kohmoto, K. et al., *Eur. J. Biochem.*, vol. 138; 1984, pp. 227-237.
Talamantes, E. et al., *Fed. Proc.*, vol. 39, 1980, pp. 2582-2587.
Colosi, P. et al., *Proc. Natl. Acad. Sci. U.S.A.*, vol. 79, Feb. 1982, pp. 771-775.
Soares, M. J. et al., *Endocrinology*, vol. 112, No. 4, 1983, pp. 1313-1317.
Robertson, M. C. et al., *Endocrinology*, vol. 108, 1981, pp. 2388-2390.
Duckworth, M. L. et al., *Endocrinology*, vol. 112, Abstract No. 938, 1983.
Linzer, D. I. H. et al., *Proc. Natl. Acad. Sci. U.S.A.*, vol. 80, Jul. 1983, pp. 4271-4275.
Cochran, B. H. et al., *Cell*, vol. 33, Jul. 1983, pp. 939-947.
Kelly, K. K. et al., *Cell*, vol. 35, Dec. (part 2), 1983, pp. 603-610.
Hirschhorn, R. R. et al., *Proc. Natl. Acad. Sci. U.S.A.*, vol. 81, Oct. 1984, pp. 6004-6008.
Linzer, D. H. et al., Abstract of Paper Presented at Cold Spring Harbor Laboratory Symposium On Cell Proliferation & Cancer, Sep. 8-13, 1983, p. 55.
Linzer, D. I. H. et al., *Proc. Natl. Acad. Sci. U.S.A.*, vol. 81, No. 14, Jul. 1984, pp. 4255-4259.
Nilsen-Hamilton, M. et al., *Cell*, vol. 20, May 1980, pp. 19-28.
Pledger, W. J. et al., *Proc. Natl. Acad. Sci. U.S.A.*, vol. 78, No. 7, Jul. 1981, pp. 4358-4362.
Thomas, G. et al., *Proc. Natl. Acad. Sci. U.S.A.*, vol. 78, No. 9, Sep. 1981, pp. 5712-5716.

*Primary Examiner*—Charles F. Warren
*Assistant Examiner*—Jeremy M. Jay
*Attorney, Agent, or Firm*—Banner, Birch, McKie & Beckett

[57] ABSTRACT

Proliferin, a growth-related hormone of the prolactin-growth hormone family is provided, as well as DNA molecules encoding proliferin and methods of expressing the DNA molecules in vivo. Methods of probing for proliferin encoding DNA are also provided.

18 Claims, 4 Drawing Sheets

```
       Met Leu Pro Ser Leu Ile Gln Pro Cys Ser Trp Ile Leu Leu Leu Leu Val Asn Ser Ser Leu Leu Trp Lys Asn
  1 AGAG ATG CTC CCT TCT TTG ATT CAA CCA TGC TCC TGG ATA CTG CTC CTA CTA CTG GTG AAC AGC TCG TTA TTG TGG AAG AAT   82

Val Ala Ser Phe Pro Met Cys Ala Met Arg Asn Gly Arg Cys Phe Met Ser Phe Glu Asp Thr Phe Glu Leu Ala Gly Ser
 83 GTT GCC TCA TTT CCC ATG TGT GCA ATG AGG AAT GGT CGT TGC TTT ATG TCC TTT GAA GAC ACA TTT GAA TTA GCC GGC AGT  163

Leu Ser His Asn Ile Ser Ile Glu Val Ser Glu Leu Phe Thr Glu Phe Glu Lys His Tyr Ser Asn Val Ser Gly Leu Arg
164 TTG TCT CAT AAT ATC AGT ATA GAA GTT TCA GAA CTG TTC ACT GAA TTT GAA AAA CAT TAT TCT AAC GTG TCT GGG CTC AGA  244

Asp Lys Ser Pro Met Arg Cys Asn Thr Ser Phe Leu Pro Thr Pro Glu Asn Lys Glu Gln Ala Arg Leu Thr His Tyr Ser
245 GAC AAA AGC CCG ATG AGA TGC AAT ACT TCT TTC CTT CCA ACT CCA GAA AAC AAG GAA CAA GCC AGG CTC ACA CAC TAT TCA  325

Ala Leu Leu Lys Ser Gly Ala Met Ile Leu Asp Ala Trp Glu Ser Pro Leu Asp Asp Leu Val Ser Glu Leu Ser Thr Ile
326 GCT CTT CTG AAA TCA GGA GCC ATG ATT TTG GAT GCC TGG GAA AGC CCT CTG GAC GAT CTA GTG AGT GAA TTA TCT ACC ATA  406

Lys Asn Val Pro Asp Ile Ile Ile Ser Lys Ala Thr Asp Ile Lys Lys Lys Ile Asn Ala Val Arg Asn Gly Val Asn Ala
407 AAA AAT GTC CCT GAT ATA ATC ATC TCC AAA GCC ACA GAC ATA AAG AAA AAG ATC AAC GCA GTC CGG AAC GGG GTT AAT GCC  487

Leu Met Ser Thr Met Leu Gln Asn Gly Asp Glu Glu Lys Lys Asn Pro Ala Trp Phe Leu Gln Ser Asp Asn Glu Asp Ala
488 CTC ATG AGC ACC ATG CTT CAG AAT GGA GAT GAA GAA AAG AAG AAC CCT GCC TGG TTC TTG CAA TCT GAC AAT GAA GAT GCT  568

Arg Ile His Ser Leu Tyr Gly Met Ile Ser Cys Leu Asp Asn Asp Phe Lys Lys Val Asp Ile Tyr Leu Asn Val Leu Lys
569 CGC ATT CAT TCT TTA TAT GGC ATG ATC AGC TGC CTA GAC AAT GAC TTT AAG AAG GTT GAT ATT TAT CTC AAC GTC CTG AAG  649

Cys Tyr Met Leu Lys Ile Asp Asn Cys STOP
650 TGT TAC ATG TTA AAA ATA GAT AAC TGC TGA TATTTCTTTCATGTGCTCTGCTTCTGAAATATCATGTAATATCCTTTCAATTTGTATCTTTTGAAT  745

746 TTGTTGTTGACTCATTTAAAAATAAAAAGTAGCTCTCAGAAATATA   791
```

```
    Met Leu Pro Ser Leu Ile Gln Pro Cys Ser Trp Ile Leu Leu Leu Leu Val Asn Ser Ser Leu Leu Trp Lys Asn
1   AGAG ATG CTC CCT TCT TTG ATT CAA CCA TGC TCC TGG ATA CTG CTC CTA CTG GTG AAC AGC TCG TTA TTG TGG AAG AAT      82

Val Ala Ser Phe Pro Met Cys Ala Met Arg Asn Gly Arg Cys Phe Met Ser Phe Glu Asp Thr Phe Glu Leu Ala Gly Ser
83  GTT GCC TCA TTT CCC ATG TGT GCA ATG AGG AAT GGT CGT TGC TTT ATG TCC TTT GAA GAC ACA TTT GAA TTA GCC GGC AGT   163

Leu Ser His Asn Ile Ser Ile Glu Val Ser Glu Phe The Glu Phe Glu Lys His Tyr Ser Asn Val Ser Gly Leu Arg
164 TTG TCT CAT AAT ATC AGT ATA GAA GTT TCA GAA CTG TTC ACT GAA TTT GAA AAA CAT TAT TCT AAC GTG TCT GGG CTC AGA   244

Asp Lys Ser Pro Met Arg Cys Asn Thr Ser Phe Leu Pro Thr Pro Glu Asn Lys Glu Gln Ala Arg Leu Thr His Tyr Ser
245 GAC AAA AGC CCC ATG AGA TGC AAT ACT TCT TTC CTT CCA ACT CCA GAA AAC AAG GAA CAA GCC AGG CTC ACA CAC TAT TCA   325

Ala Leu Leu Lys Ser Gly Ala Met Ile Leu Asp Ala Trp Glu Ser Pro Leu Asp Asp Leu Val Ser Glu Thr Thr Ile
326 GCT CTT CTG AAA TCA GGA GCC ATG ATT TTG GAT GCC TGG GAA AGC CCT CTG GAC GAT CTA GTG AGT GAA TTA ACC ATA       406

Lys Asn Val Pro Asp Ile Ile Ser Lys Ala Thr Asp Ile Lys Lys Ile Asn Ala Val Arg Asn Gly Val Asn Ala
407 AAA AAT GTC CCT GAT ATA ATC TCC AAA GCC ACA GAC ATA AAG AAG ATC AAC GCA GTC CGG AAC GGG GTT AAT GCC           487

Leu Met Ser Thr Met Leu Gln Asn Gly Asp Glu Glu Lys Asn Pro Ala Trp Phe Leu Gln Ser Asp Asn Glu Asp Ala
488 CTC ATG AGC ACC ATG CTT CAG AAT GGA GAT GAA GAA AAG AAC CCT GCC TGG TTC TTG CAA TCT GAC AAT GAA GAT GCT       568

Arg Ile His Ser Leu Tyr Gly Met Ile Ser Cys Leu Asn Asp Asn Asp Phe Lys Lys Val Asp Ile Tyr Leu Asn Val Lys
569 CGC ATT CAT TCT TTA TAT GGC ATG ATC AGC TGC CTA GAC AAT GAC TTT AAG AAG GTT GAT ATT TAT CTC AAC GTC CTG AAG   649

Cys Tyr Met Leu Lys Ile Asp Asn Cys STOP
650 TGT TAC ATG TTA AAA ATA GAT AAC TGC TGA   TATTTCTTTCATGTGCTCGTGCTTCTGAAATATCATGTAATATCCTTTCAATTGTATCTTTTGAAT   745

746 TTGTTGTTGACTCATTTAAAAATAAAAAGTAGCTCTCAGAAATATA   791
```

```
                        10                 20
          *        *   *   * * * *   *    * *       *   *
bPRL    M D S K G S S Q K G S R L L L L L V V S N L L L C Q G V V S
mPLF    M - L P S L I Q P C S W I L L L L L V N S S L L W K N V A S
bGH     M M A A G - - P R T S L L L A F A L L - C L P W T Q V V G[A]
        *          *         *   *       *              *

30              40              50
           *   *           *   *     *       *   *         * *   *
bPRL    [T]P V C P N G P G N C Q V S L R D L F D R A V M V S H Y I H
mPLF    F P M C A M R N G R C F M S F E D T F E L A G S L S H N I S
bGH     F P - - A M - - - - - - - - S L S G L F A N A V L R A Q L H
        * *       * *                   *         *       *

60              70              80
                * *       *   * *     *   *           *
bPRL    D L S S E M F N E F D K R Y - - - A Q G K G F I T M A L N S
mPLF    I E V S E L F T E F E K H Y - - - S N V S G L R D K S P M R
bGH     Q L A A D T F K E F E R T Y I P E G Q R Y S I Q N T Q V A F
                  *   * * *       *

90              100             110
             *   * *   * * * * *   * * * *     * *       *
bPRL    C H T S S L P T P E D K E Q A Q Q T H H E V L M S L I L G L
mPLF    C N T S F L P T P E N K E Q A R L T H Y S A L L K S G A M I
bGH     C F S E T I P A P T G K N E A Q Q K S D L E L L R I S L L L
        *           *       *   *                       * *

120             130             140
             *       *     * *     * *   *         * *   *   *   *
bPRL    L R S W N D P L Y H L V T E V R G M K G A P D A I L S R A I
mPLF    L D A W E S P L D D L V S E L S T I K N V P D I I I S K A T
bGH     I Q S W L G P L Q F L - S R V F T N S L V F G T S D - R V Y
              *       * *     *   *         *       *

150             160             170
             *               *                           *
bPRL    E I E E E N K R L L E G M E M I F G Q V I P G A K E T E P Y
mPLF    D I K K K I N A V R N G V N A L M S T M L Q N G D E E K K N
bGH     E - - - K L K D L E E G I L A L M R E L E D G T P R A G Q I
                  *             *       * * *

180             190             200
           *   *               * *       * * * *         *           * *
bPRL    P V W S G L P S - L Q T K D E D A R Y S A F Y N L L H C L R
mPLF    P A W F - - - - - L Q S D N E D A R I H S L Y G M I S C L D
bGH     L K Q T Y D K F D T N M R S D D A L L K N - Y G L L S C F R
                                                  * *       * *   * *

210             220
               *   *   * * *       *   *               * *
bPRL    R D S S K I D T Y L K L L N C R I I Y N N N C
mPLF    N D F K K V D I Y L N V L K C Y M L K I D N C
bGH     K D L H K T E T Y L R V M K C R R F G E A S C A F
            *           *     * *   *   * *                       *
```

GROWTH-RELATED HORMONES

The invention described herein was made with Government support under a grant or award from the Department of Health and Human Services. The Government has certain rights in this invention.

TECHNICAL FIELD

The present invention is directed to proliferin, a growth-related hormone of the prolactin-growth hormone family, DNA molecules encoding proliferin and genetic engineering methods of producing proliferin.

BACKGROUND OF THE INVENTION

Prolactin (PRL), growth hormone (GH) and placental lactogen (PL, also called chorionic somatomammotropin) comprise a recognized family of polypeptide hormones that are closely related in structure, function and immunochemistry. All three members of this prolactin-growth hormone family are of similar size (190 to 199 amino acids among various species) and are similar in protein structure. For example, each hormone has a single homologous tryptophan residue at about locus 85 (GH and PL) or 90 (PRL), and two homologous disulfide bonds. The family members also each contain four internal regions of homology which are themselves homologous among the three hormones. Regarding function, all three hormones possess lactogenic and growth-promoting activities. Based upon these observed close structural and functional relationships, it has been postulated that the three hormones arose by duplication of an ancestral hormone gene. See generally, Miller and Eberhardt, 1983, Endocrin. Rev. 4: 97-130.

Due to the medical and veterinary utility of hormones in the prolactin-growth hormone family, the identification of new hormones within this family is desirable.

SUMMARY OF THE INVENTION

It is an object of the present invention to provide mammalian proliferin, a new member of the prolactin-growth hormone family.

It is also an object of the present invention to provide DNA molecules encoding the amino acid sequence of mammalian proliferin.

A further object of the present invention is to provide a DNA molecule containing a coding sequence for mammalian proliferin that can be expressed in a procaryotic or eucaryotic cell.

Another object of the present invention is to provide a method of producing mammalian proliferin by expressing the above DNA molecules in vivo.

Yet another object of the present invention is to provide a method of making a cDNA molecule that encodes an amino acid sequence of mammalian proliferin.

These and other objects of the present invention are achieved by one or more of the following embodiments.

In one embodiment, the present invention provides a DNA molecule containing a coding sequence free of introns for the amino acid sequence of mammalian proliferin.

The present invention also provides a DNA molecule containing a coding sequence capable of being transcribed and translated in a procaryote into a protein containing the amino acid sequence of mammalian proliferin.

In another embodiment, the present invention provides a method of producing a protein having the amino acid sequence of mammalian proliferin comprising transcribing and translating in vivo the above DNA molecules into a polypeptide containing said amino acid sequence and removing the leader sequence, if any, from said polypeptide to provide said protein.

Still another embodiment of the present invention provides the plasmid PLF-1 contained in the E coli strain deposited under ATCC Accession No. 39721.

In yet another embodiment, the present invention provides a method of identifying a cDNA molecule encoding the amino acid sequence of mammalian proliferin comprising: (a) making a cDNA library from mRNA isolated from growing or proliferating cells from a first mammalian species; (b) selecting cDNA clones from said cDNA library that hybridize to at least a portion of a DNA molecule containing part or all of the coding sequence for proliferin from a second mammalian species; and (c) determining the amino acid sequence encoded by said selected cDNA clones.

In still another embodiment, the present invention provides a cell-free composition comprising mammalian proliferin.

DESCRIPTION OF THE DRAWINGS

FIG. 1 shows the nucleotide sequence of cDNA (and the predicted amino acid sequence encoded thereby) for a mammalian proliferin and its signal or leader sequence.

FIG. 3 is a comparison of the amino acid sequence of bovine prolactin, murine proliferin and bovine growth hormone.

DETAILED DESCRIPTION OF THE INVENTION

Figure 2:
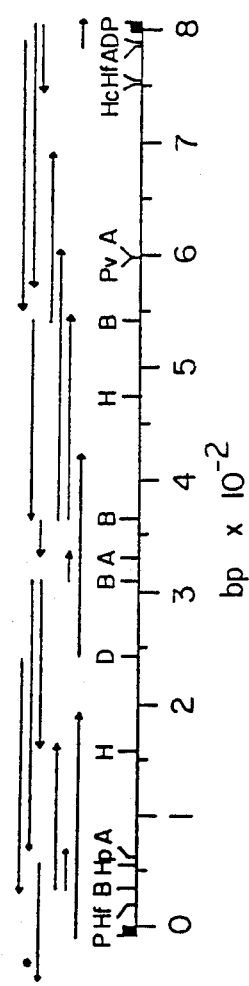
FIG. 2 is a restriction map of plamsid PLF-1 which contains the cDNA molecule of FIG. 1.

A new member of the prolactin-growth hormone family, which was known to consist of prolactin, growth hormone and placental lactogen, has been discovered. This new mammalian hormone, proliferin (PLF), exhibits significant homology to prolactin, including prolactin's characteristic cysteine and tryptophan residues located in essentially the same positions. Unlike prolactin and growth hormone, however, proliferin messenger RNA (mRNA) has not been found in any detectable quantities in the anterior pituitary of mammals such as mice. Rather, proliferin mRNA has been found in certain types of growing or prolifering cells, such as some fibroblastic and malignant cell lines, and placental tissue. The mature protein portion of mammalian proliferin has an amino acid residue mass in the general range found for other members of the prolactin-growth hormone family, namely about 22,000 to about 23,000, and may be glycosylated in the mature hormone form.

While substantial homology will be found between the amino acid sequence of mammalian proliferins and the other members of the prolactin-growth hormone family whose sequences are known, mammalian proliferins will be most homologous to (but not identical to) prolactins. From the sequence data available on placental lactogens, human placental lactogen, for example, is most homologous to growth hormone. Based upon interspecies homology of prolactins and growth hormones, the degree of homology between proliferin of a first species and proliferin of a second species will be approximated by the degree of homology between prolactins from the first and second species. Furthermore, the degree of homology between the proliferins of the first and second species will generally be higher than the degree of homology between the first species' proliferin and prolactin.

Proliferin, being a member of the prolactin-growth hormone family, doubtless has biological activities related to the biological activities of prolactin, growth hormone and placental lactogen. Thus, proliferin is of obvious interest in the medical and veterinary arts (e.g., regulating or stimulating cell growth, proliferation, and related functions of target tissues). Proliferin may also prove to have additional activities not shared with other members of the prolactin-growth hormone family.

An illustrative example of mammalian proliferin is murine proliferin (mPLF). A complementary DNA (cDNA) molecule containing the coding sequence of mPLF is provided by the present invention. The cDNA molecule, along with the amino acid sequence encoded thereby, is shown in FIG. 1. This cDNA molecule is contained in plasmid PLF-1 which in turn is available in an *E. coli* strain MM294 deposited with the American Type Culture Collection (ATCC), 12301 Parklawn Drive, Rockville, Md. 20852, on May 31, 1984, and assigned ATCC Accession No. 39721.

All or part of the cDNA portion of the PLF-1 plasmid (as well as homologous synthetic oligonucleotides) can be employed in the expression of mammalian proliferin protein or as a probe to identify cDNA from other species that encode mammalian proliferin. The complete sequence shown in FIG. 1 is murine preproliferin; i.e., proliferin protein and its leader sequence. One skilled in the art can determine the end of the leader sequence, for example, by comparing the sequence to known leader sequences of closely related hormones, such as prolactins or proliferins, or from the empirical rules in Von Heijne, 1983, *Eur. J. Biochem.* 133: 17–21. Those empirical rules indicate that about the first twenty-nine encoded amino acids constitute the signal or leader sequence. Thus, it is expected that the mature mPLF polypeptide would be produced by cleavage of the leader sequence after the serine residue at position twenty-nine. Of course, it is known that the addition or deletion of a few amino acids from a protein can be made while leaving the biological activity substantially unaffected and such modifications of amino acid sequences encoded by the claimed DNA molecules can be made without departing from the spirit of the present invention. The naturally occurring form of mammalian proliferin will require the elimination of the leader sequence from the polypeptide encoded and expressed by the cDNA molecule and (depending upon the species) glycosylation at one or more asn-x-ser or asn-x-thr regions. For expression in vivo, the nucleotide sequence encoding the leader sequence could be removed from the DNA molecule. Expression of DNA molecules containing the coding sequence for mammalian proliferin will be discussed further below.

The proliferin protein is encoded in nature by a gene in eucaryotic chromosomal DNA containing interrupting sequences (i.e., introns) within the coding sequence. While eucaryotic cells possess biochemical mechanisms for transcribing and translating coding sequences (exons) without ultimately expressing a protein containing the sequences encoded by introns, procaryotic cells do not have such mechanisms. Thus, the present invention provides a DNA molecule containing the coding sequences of mammalian proliferin, but in a form free of introns and thus capable of expression (i.e., transcription and translation) by a procaryote into a polypeptide containing the amino acid sequence of mammalian proliferin. In one embodiment, the DNA molecule encodes only the amino acid sequence found in mature proliferin. In another embodiment, the DNA molecules also contains a coding sequence for a leader sequence; i.e., preproliferin.

DNA molecules capable of expressing in a procaryote a protein containing the amino acid sequence of the mammalian proliferin can be produced by making cDNA transcripts of mRNA which has in turn been transcribed from a gene, such as a eucaryotic gene, encoding mammalian proliferin. Eucaryotic processed mRNA is free of introns and the cDNA transcript is suitable, therefore, for expression in procaryotic cells. The general techniques for making cDNA copies of mRNA are well known to those of skill in the art. See, e.g., U.S. Pat. Nos. 4,446,235; 4,440,859; 4,433,140; 4,431,740; 4,370,417; and 4,363,877. The method employed to create the cDNA molecule of mPLF found in plasmid PLF-1 is described in detail below.

Segments of the cDNA molecule in PLF-1 are valuable probes that can be used to isolate the cDNA copies of mammalian proliferin from other species. See, e.g., U.S. Pat. No. 4,446,235 and British Patent Specification GB No. 2,215,409. Analogous sequences derived from other mammalian proliferins can also be used. As a source of mRNA, appropriate growing and/or proliferating cells from a first mammalian species are employed. The source of the first species' cells can be, for example, a human, bovine, equine, ovine or porcine source, and candidates for appropriate cells are placental tissue, fibrobastic cell lines or malignant cell lines. Isolated mRNA is transcribed in vitro into cDNA molecules which are cloned into an approprite vector, such as a plasmid, to create a cDNA library. Sequences homologous to a cDNA coding sequence for PLF from a second species (e.g., mPLF cDNA) is then used as a probe to identify likely cDNA molecules from the library. The nucleotide sequence of cDNA clones detected by hybridization to a probe can be determined and the amino acid sequence predicted.

Based upon the amino acid sequence predicted from a particular cDNA molecule, one skilled in the art can readily identify those molecules encoding proliferin. First, the molecular weight and general amino acid sequence homology to the members of the prolactin-growth hormone family (i.e., prolactin, growth hormone, proliferin and placental lactogen) will identify the cDNA molecule as encoding a hormone of that family to one skilled in the art. See, e.g., Miller and Eberhardt, 1983, *Endocrine Rev.* 4: 97–130. Second, particular aspects of the amino acid sequence will readily identify a proliferin-encoding cDNA molecule from the first species. A proliferin amino acid sequence will be more homologous to prolactins than growth hormones, and will be most homologous to other proliferins. For example, the proliferin sequence of the first species will be more homologous to the proliferin sequence of a second species (e.g., murine) than to the prolactin sequences from either the first or second species. The proliferin protein will also have cysteine residues in essentially the same positions as those found in murine proliferin and murine prolactin. The proliferin from the first species will also most likely have tryptophan residues at essentially the same positions as other proliferins and prolactins. Tryptophan number may vary, however, as has been found for murine prolactin. If sufficient mature hormone is available, it is desirable to test for a biological activity related to that of the proliferin-prolactin-growth hormone-placental lactogen family to characterize further the hormone. Finally, the cell source of mRNA may also be considered; proliferin mRNA is generally found in growing or proliferating cells or tissues. One skilled in the art can readily make the above comparison. See, e.g., Kohmoto et al., 1984, *Eur. J. Biochem.* 138: 227–237.

The cDNA molecules of the present invention can be expressed in vivo in either procaryotes or eucaryotes. Methods of expressing cDNA molecules containing eucaryotic coding sequences in procaryotes are well known in the art. See, e.g., U.S. Pat. Nos. 4,440,859; 4,436,815; 4,431,740; 4,431,739; 4,428,941; 4,425,437; 4,418,149; 4,411,994; 4,366,246; and 4,342,832. See also, British Patent Specifications GB No. 2,121,054; GB No. 2,008,123; GB No. 2,007,67; GB No. 2,007,675; and European Patent Specification No. 103,395.

Preferably, the cDNA molecule lacking the mammalian leader sequence is inserted into a procaryotic expression vector (e.g., a plasmid or bacteriophage) at a position where it is controlled by a procaryotic regulatory region (i.e., promoter, operator, etc.) and the start codon of the coding sequence is also at the correct distance from the ribosome binding sequence. A procaryotic leader sequence may be desirable to promote extra-cellular transport of the protein or to protect it from proteolytic enzymes. See, e.g., U.S. Pat. Nos. 4,431,739; 4,425,437. Numerous procaryotic expression vectors are known in the art, such as plasmid PλS. See Reed, 1983, *Meth. Enzym.* 100: 191–196. The selection of an appropriate expression vector is within the skill of the art. The protein recovered from the procaryote may require in vitro processing to make bioactive proliferin; i.e., cleavage of the leader sequence, if any, and glycosylation, if appropriate.

Although the cDNA molecules provided by the present invention are especially adapted for expression in procaryotes, it is still advantageous to express cDNA molecules in eucaryotic cells that contain the enzymes for cleavage of leader sequences and glycosylation. Methods of expressing foreign DNA in eucaryotic cells are also known in the art. For example, it is known how to express foreign DNA encoding proteins in yeast. See, e.g., U.S. Pat. Nos. 4,446,235; 4,443,539; 4,430,428. See also European Patent Specification Nos. 103,409; 100,561; 096,491. Eucaryotic cells can also be cotransformed with foreign cDNA encoding a desired protein, such as PLF, and a second foreign DNA molecule encoding a selectable phenotype, such as the herpes simplex thymidine kinase gene. See, e.g., U.S. Pat. No. 4,399,216. Another method is to use a eucaryotic viral vector, such as simian virus 40 (SV40) or bovine papilloma virus, to infect transiently or to transform eucaryotic cells and express the protein. See, e.g., U.S. Pat. Nos. 4,442,205; 4,419,446. See also *Eucaryotic Viral Vectors* (Cold Spring Harbor Laboratory, Gluzman ed., 1982); Pavlakis et al., 1981, *Proc. Natl. Acad. Sci. USA* 78: 7398.

The DNA molecules provided by the present invention can also be used as sources for probes that can be employed to isolate eucaryotic chromosomal or genomic DNA encoding mammalian proliferin. Insertion of these genomic DNA molecules into retrovirus vectors can be used to generate cDNA-like contiguous proliferin coding segments free of introns. See, e.g., Shimotohno and Temin, 1982, *Nature* (London) 299: 265–268. These intron-free DNA molecules can be employed in the above procaryotic or eucaryotic expression vectors. Alternatively, the isolated genomic DNA can then be used directly to transform a eucaryotic cell with or without eucaryotic vectors to produce a eucaryotic cell containing an exogenous or new DNA segment that can be transcribed and translated by the eucaryotic cell into mature proliferin. Transformation is defined as the alteration of a recipient cell's genotype by the introduction of new DNA by any known method, such as viral vectors, yeast plasmids, $CaCl_2$ coprecipitation or microinjection. See, e.g., U.S. Pat. No. 4,446,235. The cell can be transformed with proliferin DNA from a second species or with additional copies of proliferin genes from the same species. If the cell is from a culturable cell line (e.g., fibroblastic or malignant cells), the transformed cell can be clonally expanded into a transformed cell line.

Whether procaryotic or eucaryotic cells are employed to express proliferin, it is within the skill of the art to recover proliferin in a soluble, cell-free form; i.e., not associated with cells or tissues. Such cell-free compositions of proliferin can be substantially purified and/or concentrated by techniques known in the art or left as crude preparations.

While the practice of the present invention requires the application of recombinant DNA technology, such techniques are within the skill of those in art. See e.g., *Molecular Cloning: A Laboratory Manual* (Cold Spring Harbor Labratory, Maniatis, Fritsch & Sambrook eds., 1982); Linzer and Nathans, 1983, *Proc. Natl. Acad. Sci. USA* 80: 4271–4275; Linzer and Nathans in *Cancer Cells 1: The Transformed Phenotype*, pp. 111–115 (Cold Spring Harbor Labratory 1984). These, as well as all the other references cited herein, are expressly incorporated by reference.

Below are specific embodiments of the present invention which are provided, not as limitations thereon,, but for illustrative purposes only.

EXPERIMENTAL METHODS

Enzymes and Growth Factors

All enzymes were purchased from commercial sources, except for avian myeloblastosis virus reverse transcriptase and *Escherichia coli* DNA polymerase I, which were kindly provided by J. Beard and P. Englund, respectively. Purified and titered platelet-derived growth factor (PDGF) was the generous gift of E. Raines and R. Ross (16).

Cell Culture

BALB/c 3T3 (Todaro et al., 1963, *J. Cell Biol.* 17: 299–313) and C3H 10T1/2 (Reznikoff, et al., 1973, *Canc. Res.* 33: 3231) cells were grown in Eagle's minimal essential medium with Earl's salts (GIBCO) supplemented with penicillin (10 units/ml), streptomycin (10 units/ml), glutamine (2 mM), and fetal bovine serum to 10% (MEM-10). Resting cultures were obtained by growing cells to confluence, feeding with minimal essential medium containing 0.5% (MEM-0.5) or 2% (MEM-2) fetal bovine serum, and maintaining the cells in low serum for at least two days. Resting cells were stimulated by feeding with minimal essential culture containing 20% fetal bovine serum (MEM-20), by adding PDGF directly to the medium at a final concentration of 11 ng/ml, or by infecting with CsCl-banded simian virus 40 (SV40) in MEM-0.5 at a multiplicity of 50 plaque-forming units per cell. SV40-transformed BALB/c 3T3 cell lines SVB 10-1 and SVB 10-2 were selected as foci growing in MEM-10 and MEM-2, respectively, by Phoebe Mounts. Krebs ascites carcinoma cells were grown in the peritoneal cavity of BALB/c mice and harvested 10 days after inoculation.

Purification of RNA

Krebs ascites carcinoma cells (from American Type Culture Collection) were isolated from the peritoneal cavity of BALB/c mice 10 days after injection. These cells, as well as BALB/c 3T3 and C3H 10T1/2 cells, were lysed in guanidinium thiocyanate solution (Chirgwin et al., 1979, *Biochemistry* 18: 5294–5299), and the RNA was pelleted through a CsCl cushion (Glisin et al., 1974, *Biochemistry* 13: 2633–2637). 3T3 cell RNA was also prepared from the cytoplasmic fraction of cells lysed in 10 mM Tris-HCl, pH 7.4/10 mM NaCl/2.5 mM $MgCl_2$, 0.5% Nonidet P-40 and digested with proteinase K at 100 μg/ml in the presence of 0.5% NaDodSO$_4$. Poly(A)+ RNA was selected by two cycles of binding to oligo(dT)-cellulose (Aviv and Leder, 1972, *Proc. Natl. Acad. Sci. USA* 69: 1408–1412).

Construction of the cDNA Library

Double-stranded cDNA was synthesized from approximately 20 μg of poly(A)+ RNA (Wickens et al., 1978, *J. Biol. Chem.* 253: 2483–2495) and inserted by G and C homopolymer tails (Roychoudhury et al., 1976 *Nucleic Acid Res.* 3: 101–116; Otsuka, 1981, *Gene* 13: 339–346) into the unique Pst I site of the plasmid pKP43 [a 967-base-pair (bp) deletion mutant of pBR322 constructed and provided by K. Penden]. Annealed vector cDNA was used to transform competent *E. coli* MM294 cells (Meselon and Yuan, 1968, *Nature* (London) 217: 1110–1114) to tetracycline resistance (Lederberg and Cohen, 1974, *J. Bacteriol.* 119: 1072–1074).

Colony Hybridization

Individual colonies were grown in L broth containing tetracycline at 4 ug/ml in 96-well microtiter trays and transferred to filters (GeneScreen, New England Nuclear) with a replica tool. Colonies were grown on the filters and the plasmid DNA's were amplified on L agar plates containing chloramphenicol at 250 ug/ml (Clewell, 1972, *J. Bacteriol.* 110: 667–676). Cells were lysed with 0.5M NaOH, and the filters were washed with 1.0M Tris-HCl, pH 7.4, and with 0.5M Tris-HCl, pH 7.4/1.5M NaCl (Grunstein and Hogness, 1975, *Proc. Natl. Acad. Sci. USA* 72: 3961–3965). After baking and incubating as described (Peden et al., 1982, *Cell* 31: 71–80), the filters were hybridized with cDNA probes at $1 \times 10^6$ dpm/ml for 48–72 hr. at 68° C. $^{32}$P-Labeled cDNA probes were synthesized to approximately $5 \times 10^9$ dpm/ug from cytoplasmic poly(A)+ RNA from confluent cells maintained in MEM-0.5 for six days or from subconfluent cultures that were proliferating in MEM-10. Filters were washed (Peden et al., 1982, supra) and autoradiographed (Laskey and Mills, 1977, *FEBS Lett.* 82: 314–316).

High Density Colony Hybridization

The cDNA library was grown on nitrocellulose filters on agar plates containing 6 ug/ml tetracycline, and replica filters were prepared by the procedure of Hanahan and Meselson, 1980, *Gene* 10: 63–67. For the high density screen, each 88 mm × 88 mm filter contained approximately 50,000 colonies. The bacterial colonies on the replica filters were lysed (Id.), and the filters were baked and incubated prior to hybridization as described (Peden et al., 1982, *Cell* 31: 71–80). Hybridizations were performed for 12–18 hr at 37° in a solution containing 1M NaCl, 50 mM Tris-HCl, pH 7.4, 5 mM EDTA, 0.5% NaDodSO$_4$ and 0.2% bovine serum albumin, 0.2% Ficoll, 0.2% polyvinylpyrrolidone (Denhardt, 1966, *Biochem. Biophys. Res. Commun.* 23: 641–652), 10 ug/ml denatured *E. coli* DNA, and $1 \times 10^6$ dpm/ml of kinase-labeled oligonucleotide. The filters were washed in 0.9M NaCl/0.09M sodium citrate at 0° C. with several changes for a total of 1 hr, and then in fresh solution of the same composition at 37° C. for two 10 minute periods (Wallace et al., 1981, *Nucleic Acids Res.* 9: 879–894). After drying, the filters were exposed to X-ray film. Hybridizing regions were picked and rescreened at low density by the same procedure. Finally, individual colonies were picked into microwells and screened as described above.

DOT BLOT HYBRIDIZATION

Plasmid DNAs, linearized with BamHI restriction endonuclease, were denatured by heating in 0.1M NaOH for 15 minutes at 100° C. Each sample was neutralized with an equal volume of 45 mM NaOAc, pH 4.8, 2.5M NaCl and immediately spotted on a nitrocellulose filter using a blotting manifold (Bethesda Research Laboratories). These dot blots were processed as described for the colony screen. The extent of hybridization was first analyzed by autoradiography and then quantified by liquid scintillation counting.

PREPARATION OF DNA

Recombinant plasmid DNAs were prepared on a small scale (Holmes and Quigley, 1981, *Anal. Biochem.* 114: 193–197) or were purified by CsCl/ethidium bromide centrifugation (Peden et al., 1982, supra). Ethidium bromide was extracted with isobutanol and CsCl was removed by dialysis or ethanol precipitation. The rat prolactin cDNA clone PRL-2 (Gubbins et al., 1979, *Nucleic Acids Res.* 6: 915–930; Gubbins et al., 1980, *J. Biol. Chem.* 255: 8655–8662) was the generous gift of R. Maurer. BALB/c liver DNA was kindly provided by K. Peden. The chicken α-tubulin cDNA clone (Cleveland et al., 1980, *Cell* 20: 95–105) was the generous gift of D. Cleveland.

Defined olignonucleotides were synthesized with an Applied Biosystems 380A DNA synthesizer, and the final products were purified by high performance liquid chromatography. Oligonucleotides were labeled with T4 polynucleotide kinase and gamma-$^{32}$P-ATP.

RNA Filter Hybridization

Denatured total cellular RNA was electrophoresed on formaldehyde agarose gels (Lehrach et al,, 1977, *Biochemistry* 16: 4743; Goldberg, 1980, *Proc. Natl. Acad. Sci. USA* 77: 5794) and transferred to nitrocellulose (Thomas, 1980, *Proc. Natl. Acad. Sci. USA*, 77: 5201). After baking under vacuum for two hours at 80° C., filters were prehybridized for three hours at 42° C. in formamide buffer (Fellous et al., 1982, *Proc. Natl. Acad. Sci. USA,* 79: 3082) and then hybridized in fresh formamide buffer containing 10 ug/ml denatured salmon sperm DNA, 5 ug/ml tRNA, and 1×10$^6$ dpm/ml of recombinant plasmid DNA nick-translated (Rigby et al., 1977, *J. Mol. Biol.,* 113: 237) to 1–2×10$^8$ dpm/ug. Hybridizations were terminated after 36–48 hours, and the filters were washed (Thomas, 1980, supra).

Mouse genomic DNA was digested with the restriction endonuclease EcoRI, extracted with phenol/chloroform, and ethanol precipitated prior to electrophoresis in 1% agarose gels. The DNA was transferred to nitrocellulose (Southern, 1975, *J. Biol. Chem.* 98: 503–517) baked, and then treated as described for colony hybridizations, except that salmon sperm DNA replaced *E. coli* DNA, and cDNA clones nick-translated (Rigby et al., 1977, *J. Biol. Chem.,* 113: 237–251) to 5×10$^8$ dpm/ug were used as probes instead of cDNA or oligonucleotides. Hybridizations with rat prolactin clone PRL-2 were carried out at 60° C. for 60 hr; filters were hybridized with the mouse proliferin clone at 67° C. for 60 hr. Filters were washed at 60° C. or 67° C., respectively, as described in Peden et al., 1982, *Cell* 31: 71–80, and then exposed for autoradiography.

DNA Sequence Analysis

The cDNA clones were end labeled by filling in 5' overhangs, left after restriction endonuclease cleavage, with the Klenow fragement of *E. coli* polymerase I and an alpha-$^{32}$-P-deoxynucleoside triphosphate. PstI 3' overhangs were labeled with alpha-$^{32}$P-cordycepin triphosphate and terminal transferase (Tu and Cohen, 1980, *Gene* 10: 177–183). Fragments labeled at one end were isolated from polyacrylamide gels, and sequenced by the method of Maxam and Gilbert, 1980, *Meth. Enzymol* 65: 499–560. The cleavage products were resolved on 8% or 20% polyacrylamide-urea gels (Sanger et al., 1978, *FEBS Lett.* 87: 107–110) and the gels were autoradiographed.

PRIMER EXTENSION

Three pmoles of kinase-labeled oligonucleotide were hybridized to 10 ug of Krebs acites carcinoma poly(A)+ RNA in 20 ul of 100 mM KCl. The mixture was heated at 75° C. for 5 min, then 42° C. for 15 min, 37° C. for 15 min, and 23° C. for 10 min, and then supplemented to 50 mM Tris-HCl, pH 8.3 (at 42° C.), 10 mM MgCl$_2$, 10 mM dithiothreitol, 1 mM each of the four deoxynucleoside triphosphates, 500 U/ml RNasin (Promega-Biotec), and 30 U reverse transcriptase (Life Sciences). The reaction was incubated for 10 min at 37°, and then for 2 hr at 42°. After phenol/chloroform extraction, the aqueous phase was loaded on a polyacrylamide gel and electrophoresed. Extended primer bands were visualized vy autoradiography of the unfixed, wet gel, and these cDNAs were eluted and sequenced (Maxam and Gilbert, 1980, *Meth. Enzymol* 65: 499–560).

Hybrid-Selected Translation

The proliferin cDNA clone (20 ug) was linearized with EcoRI, denatured in 0.1N NaOH, neutralized with an equal volume of 45 mM sodium acetate, pH 4.8, 2.5M NaCl, and spotted on nitrocellulose. After baking, the filter was washed, and hybridized to 1 mg Krebs ascites carcinoma total cellular RNA, essentially as described in *Molecular Cloning: A Laboratory Manual.,* pp. 329–341 (Maniatis et al. eds. 1982). The hybridization mixture (in 50% formamide, 20 mM Pipes, pH 6.4, 0.2% NaDodSO$_4$, 400 mM NaCl) was heated at 70° C. for 10 min., then incubated at 50° C. overnight. After washing the filter, bound RNA was eluted, extracted with phenol/chloroform, and ethanol precipitated (id.). The RNA was translated in a rabbit retriculocyte lysate, and products were resolved by SDS-polyacrylamide gel electrophoresis (Laemmli, 1970, *Nature* (London) 227: 680–685). The gel was treated with Enhance (New England Nuclear) prior to exposure.

Computer Analysis

Nucleotide sequences were compared to the sequences in the Los Alamos Data Bank using the algorithm of Wilbur and Lipman, 1983, *Natl. Acad. Sci. USA* 80: 726–730.

Mammalian Cell Tansfection

The carboxy terminal end of the PLF-1 coding sequence was modified by attaching a BamHI linker. The amino terminal coding region was then modified by the addition of a Hind-III linker. This DNA was inserted between the Hind-III and BamHI sites in the late region of simian virus 40(SV40) cloned in pBR322. Plasmid DNA was then cut with BamHI, and the SV40 portion re-circularized to generate an SV40 genome wherein the VP1 gene has been replaced by the mPLF cDNA.

Monkey cells were cotransfected with the SV40-PLF DNA and a helper SV40 lacking an intact early region. A mixed rival stock was derived from the transfected cell lysate and used to infect other monkey cells to express the proliferin protein.

EXPERIMENTAL RESULTS

Construction of a cDNA Library from Serum-Stimulated Cells

Total cellular RNA was prepared from BALB/c 3T3 tissue culture cells at 12 hours after stimulation with MEM-20. This time corresponds to the onset of DNA synthesis as indicated by the incorporation of [$^3$H]thymidine into trichloroacetic acid-insoluble material. (The maximal rate of DNA synthesis occurred 16–18 hours after the addition of serum.) The poly(A)+ RNA fraction was used as template for the synthesis of double-stranded cDNA, which was inserted into the β-lactamase gene of the plasmid pKP43. The recombinant molecules were introduced into competent E. coli, generating a cDNA library of approximately 1×10$^6$ transformants.

Screening for Growth-Related Clones

Individual ampicillin-sensitive colonies were grown overnight in liquid culture in 96-well microtiter trays. Replica filters were prepared, colonies were established on filters, and the plasmid DNA sequences were amplified by incubation of the filters in the presence of chloramphenicol. Plasmid DNA within each bacterial colony was denatured, immobilized on the filter, and hydridized to cDNA probes representing either resting or growing BALB/c 3T3 cell cytoplasmic poly(A)+ RNA. The degree of hybridization was determined by autoradiography. Colonies that hybridized preferentially to the probe made from growing cell RNA were selected for further analysis. This initial survey eliminated approximately 95% of the 3,500 colonies screened; no colonies were identified that revealed consistently greater hybridization to the resting cell probe.

DNA was prepared from each clone harboring presumptive growing cell-specific sequences, as well as from a few control clones that gave no differential colony hybridization. Individual recombinant plasmid DNAs were prepared, applied in duplicate to nitrocellulose filters, and hybridized to resting and growing cell-specific probes. Autoradiography of these filters revealed 13 clones that demonstrated preferential hybridization to the probe synthesized from growing cell RNA; these clones represent approximately 0.5% of the members of the library that were initially screened. The degree of differential hybridization of each of the 13 clones was quantified with CsCl-purified DNA dot blots. Denatured DNAs were spotted onto nitrocellulose, and the filters were hybridized to resting and growing cell-specific cDNA probes. The degree of hybridization was determined by measuring the cpm present in each dot in a liquid scintillation counter and subtracting the cpm bound to the corresponding amount of vector alone. It was evident that the cloned cDNAs were derived from mRNAs that varied in response to serum and that differ in abundance.

Serum Stimulation of RNA Production

The eight individual clones that showed the greatest relative hybridization were utilized to probe for levels of the corresponding RNA species in quiescent cells and at various times after serum stimulation. Total cellular RNA was prepared from confluent cells that had been maintained in MEM-2 and from cultures that were stimulated by feeding with MEM-20 for 6-36 hours. The RNAs were electrophoresed on formaldehyde/agarose gels, transfered to nitrocellulose, and probed with nick-translated cloned DNAs. Clones 18A2, 28H6, and 32A4 detected significant differences in the amount of the corresponding RNA present in stimulated versus nongrowing BALB/c 3T3 cell cultures. 18A2 hybridized to a single size RNA of approximately 0.7 Kilobases (kb); 28H6 detected a major RNA species of 1 kb and minor amounts of higher molecular weight RNA; and 32A4 hybridized to several RNAs. A control hybridization employing another cDNA clone (31G8) gave no differential hybridization in the colony and dot blot analyses. On the basis of intensity of hybridization to the various RNA species, it is likely that 28H6, 32A4 and 31G8 RNAs are more abundant than 18A2 RNA.

Each electrophoresis lane was traced with a densitometer, and the quantity of RNA detected at any given time was normalized to the maximum level attained for that RNA. The time course of RNA levels differed for the RNAs examined. The level of 18A2 RNA remained low for 12 hours after serum stimulation, then rose sharply to at least three times the resting cell level and remained high through the 36-hour time point. (The sharp rise corresponded temporally to the onset of DNA synthesis). By comparison, the 1-kb RNA that hybridized to the 28H6 probe increased steadily in amount to a peak at 12 hours after application of serum, reaching a level at least 15- to 20-fold higher than in resting cells. In other experiments, the 28H6 1-kb RNA was undetectable in resting cells and appeared within three hours after serum stimulation. Thus, the increase in 28H6-specific RNA preceded cellular DNA synthesis. After the 12-hour time point, 28H6 RNA decreased in quantity, again in contrast to the 18A2 RNA. The 32A4 probe revealed a more complicated pattern. A 0.6-kb RNA increased approximately three-fold to a peak level at 12 hours and then decreased. Three larger RNA species remained constant in amount, while a 0.4-kb RNA level rose to a peak at 24 hours. Patterns of RNA identical to the pattern detected by the 32A4 clone were observed by using three of the other growth-specific clones as probes.

The poly(A)+ fractions of the total cellular RNAs analyzed were also probed with the 18A2, 28H6 and 32A4 clones. The results were similar to those found for total cellular RNA. However, the higher molecular weight 28H6 RNA and the 32A4 0.4-kb and 2.9-kb bands were not detected in the poly(A)+ fraction. Because of the virtual absence of 28H6 RNA from resting cells and the marked increase in the level of this RNA just before the onset of DNA synthesis, it was decided to concentrate on 28H6 ARNA in the experiments described below.

Growth State and RNA Levels

Total cellular RNA was purified from BALB/c 3T3 cells maintained in MEM-10 and harvested at two subconfluent densities (approximately 20% and 90% confluent), during serum deprivation (1 and 2 days in MEM-0.5 after attaining confluence), and at 12 and 24 hours after feeding the 2-day-starved cultures with MEM-20. These RNAs were electrophoresed, transferred to nitrocellulose, and hybridized to a mixed probe of 28H6 plasmid DNA and an α-tubulin cDNA clone. The 1-kb RNA species that hybridized to the 28H6 cDNA was present at a high level in growing, subconfluent cell cultures. This level decreased at the higher cell density even though the cells were still in medium containing 10% serum and the cultures had not quite reached confluence. As demonstrated above, starved cultures also had a low concentration of this RNA, whereas serum-stimulated cells expressed greatly increased amounts. The serum-stimulated samples contained an increased quantity of the larger 28H6-specific RNA of 4-kb, as well. The α-tubulin 1.8-kb RNA also was present at a greater concentration in low density, actively growing cell cultures than in higher density and serum-depleted populations. Serum stimulation restored the amount of α-tubulin RNA to a quantity equal to or greater than that found in the 20% confluent cultures. It is clear, however, that the changes in the level of 28H6-specific RNA during this time course exceeded those observed for α-tubulin.

Cells were plated at low density in MEM-10 and fed on the following day with either MEM-2 or MEM-10. On each successive day, some of the dishes were harvested for the preparation of total cellular RNA, while the medium in each of the remaining dishes was replaced with fresh MEM-2 or MEM-10, respectively. Cultures fed with MEM-2 and MEM-10 continued to grow and divide at the same rate during the course of the experiment. RNA samples were obtained from cultures that were about 20%, 50%, 95% and 100% confluent. The amount of 28H6-specific RNA (both the 1-kb and 4-kb RNAs) was much greater in cells growing in 10% versus 2% serum, but the level decreased with increasing cell density in each case. Confluent cultures stimulated with fresh MEM-10 maintained a higher level of 28H6 RNA than did cultures that grew to near confluence in unchanged MEM-10. These results indicate that the level of 28H6-specific RNA varies both with the growth state or confluence of the cells and, more strikingly, with serum concentration.

Response to Defined Mitogens

To determine whether defined mitogens affected the level of 28H6 RNA, resting cultures were treated with SV40 or PDGF, each of which has been shown to stimulate the growth of mouse 3T3 cells.

Total cellular RNA was isolated from resting cultures of BALB/c 3T3 cells infected with purified SV40 virions at 6–36 hours post infection (pi), as well as from uninfected, 24-hour mock-infected, and 12-hour serum-stimulated cultures. After electrophoresis and transfer, the filter-bound RNA was probed with 28H6 DNA. SV40 infection resulted in an increase of the level of 28H6 RNA, although to a lesser extent that serum stimulation. At least part of this difference can be accounted for by the relative resistance of starved 3T3 cells to infection by SV40. Even in infections with 50 plaque-forming units per cell, less than half of the cells expressed the SV40 large tumor (T) antigen, as assayed by indirect immunofluorescence. It is evident that the time course of the change in 1-kb RNA level in response to SV40 infection was similar to that observed for serum: the amount of RNA increased rapidly from an initial low level in uninfected or mock-infected cells to a peak level by 12 hours followed by a decrease at later times.

Cell cultures grown to confluence and maintained in medium with a low concentration of serum were also stimulated by addition of purified PDGF. At 11 ng/ml [5.5 ng/ml is equivalent to stimulating Swiss 3T3 DNA synthesis with 5% calf serum] PDGF markedly stimulated resting BALB/c 3T3 cells to synthesize DNA. In two independent experiments, this concentration of PDGF elicited a high level of 28H6 RNA. The PDGF-treated cultures produced more of this RNA than did cultures fed with MEM-10 but less than cells stimulated with MEM-20.

RNA Levels in Other Cell Lines

Total cellular RNA was prepared from cultures of C3H 10T$\frac{1}{2}$ cells that were subconfluent and actively growing in MEM-10, from cultures that were fed with MEM-0.5 for two days after achieving confluence, and from these resting cultures that were stimulated with MEM-10 or MEM-20 for twelve hours. Analysis of BALB/c 3T3 cells grown under these conditions revealed a high level of 28H6 RNA in actively growing, subconfluent cultures, as well as an increase in the level of this RNA after serum stimulation of resting cultures that was dependent in magnitude on the concentration of serum. The same results were obtained with the 10T$\frac{1}{2}$ cells. Actively growing and serum stimulated cultures contained high levels of the 28H6 RNA compared to resting cell cultures, and the amount of this RNA was greater in cells treated with MEM-20 than with MEM-10. RNA was prepared from another mouse cell line, Krebs ascites carcinoma cells, that had been rapidly proliferating after intraperitoneal injection into BALB/c mice. Probing this RNA with cDNA clone 28H6 demonstrated a very high level of the 1-kb RNA, and an easily detectable amount of the 4-kb RNA.

The increase in amount of 28H6 after infection of quiescent cultures with SV40 suggested that SV40-transformed BALB/c 3T3 cells may maintain an elevated concentration of this RNA. Cultures of cell lines SVB 10-1 and 10-2 were grown from a low cell density ($1 \times 10^3$ cells/cm$^2$) to a high density ($2 \times 10^5$ cells/cm$^2$) in MEM-2 and MEM-10. RNA was prepared from cultures at these two densities as well as from two intermediate cell densities, and examined with the 28H6 cDNA clone. The SVB 10-1 cell line, which was originally selected as a focus growing in MEM-10, expressed a moderate amount of the 1-kb RNA when proliferating in MEM-10; this level of 28H6 RNA was independent of cell density, but was considerably lower than that detected in actively growing or serum-stimulated BALB/c 3T3 cells growing in the same medium. In contrast, SVB 10-1 dividing at approximately the same rate in MEM-2 failed to produce any observable 28H6 RNA. SVB 10-2, isolated as a focus in MEM-2, also gave no detectable 28H6 RNA in MEM-2 at any cell density tested; in MEM-10, these cultures contained a very low level of the 1-kb RNA are the lowest cell density, but this amount decreased rapidly below the level of detection as the cell density increased.

Nucleotide Sequence of Proliferin cDNA

By nucleotide sequence analysis, the 28H6 cDNA insert contains 422 base pairs, representing approximately the 3' half of the mRNA. To obtain a more complete cDNA, a synthetic oligonucleotide representing a 14 nucleotide long sequence from the 5' end of the 28H6 cDNA was used to probe the original cDNA library. Of $5 \times 10^5$ colonies screened, approximately 400 hybridized to the probe. Thus, this cDNA is at least 0.08% of the library. Several clones with longer cDNA inserts than clone 28H6 were isolated and partially sequenced, but none of these extended to the expected methionine codon at the translation initiation site. Therefore a second synthetic oligonucleotide, representing 5' sequences from the longest cDNA insert, was used to probe the cDNA library once more. Only 20 out of $5 \times 10^5$ colonies hybridized to this 17-nucleotide probe. One of these (designated clone PLF-1) contains a cDNA insert extending beyond the putative translation start site. A restriction map of this clone is shown in FIG. 2, together with a display of fragments sequenced. Plasmid PLF-1 is contained in *E. Coli* MM294 deposited with the ATCC under Accession No. 39721.

As shown in FIG. 1, PLF-1 cDNA has a single open reading frame, coding for a protein with 224 amino acid residues, on the assumption that the ATG beginning at nucleotide 5 is the start codon. By extension of the 17 nucleotide primer hybridized to proliferin mRNA prepared from growing Krebs ascites carcinoma cells above, an additional 37 nucleotides were sequenced; the position of the putative start codon was confirmed, and no other in-phase methionine codons were found. The translation termination codon TGA appears at nucleotides 677–679, and a polyadenylation signal AATAAA is present around nucleotide 770. The sequence of all the other proliferin cDNA clones analyzed agree with that of PLF-1, except for some heterogeneity in the site of polyadenylation.

Relationship of Proliferin to Prolactin

The first indication that proliferin is related to prolactin came from a comparison of the nucleotide sequence of 28H6 cDNA to the sequences stored in the Los Alamos DNA data bank. It was also noted that proliferin mRNA from mouse 3T3 cells or Krebs ascites carcinoma cells is about 1 kb in length, about the same size as prolactin mRNA (Maurer, 1981, *Nature* 294: 94–97). Furthermore, purification of Krebs cell proliferin mRNA by hybridization to proliferin cDNA and translation in vitro results in a polypeptide with an estimated molecular weight of 25,000, about the same as that of preprolactin (Miller et al., 1983, *Endocrine Rev.* 4: 97–130). The complete amino acid sequence of mouse prolactin has recently been published (Kohomoto et al., 1984, *Eur. J. Biochem.* 138: 227–237), however, conclusively demonstrating that mouse prolactin and proliferin are different hormones of related structure.

Figure 4:
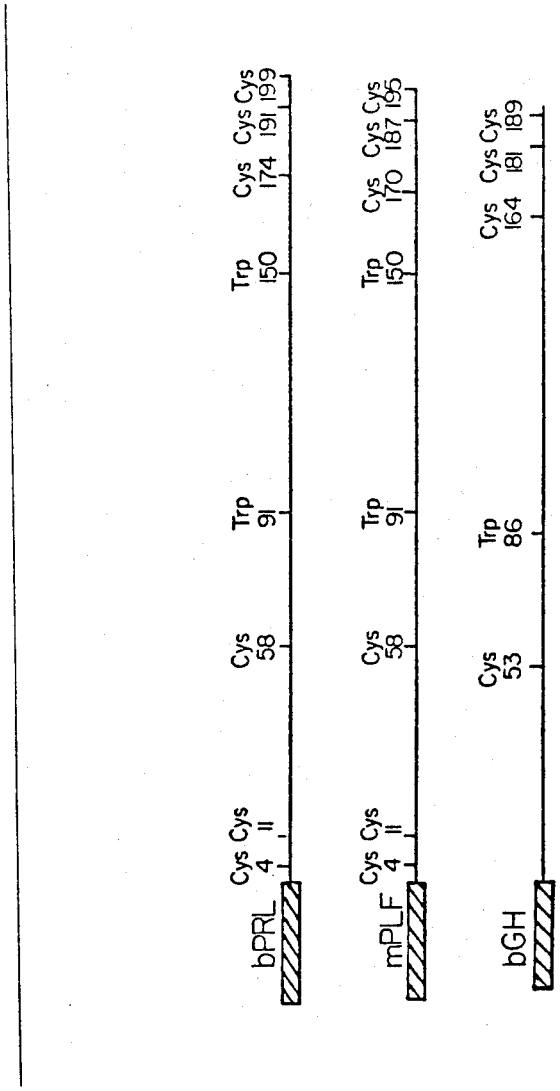
FIG. 4 shows the locations of the cysteine and tryptophan residues of murine proliferin, bovine prolactin and bovine growth hormone.

The nucleotide sequence homology between the coding regions of PLF-1 and bovine prolactin cDNA (Sasavage et al., 1982, *J. Biol. Chem.* 257: 678–681) is 55% and is reflected in the amino acid sequence comparisons of the two proteins. In FIG. 3 the predicted amino acid sequence of murine proliferin (mPLF) is compared with the sequences of bovine prolactin (bPRL) and bovine growth hormone (bGH), which is related to prolactin (Miller et al., 1983, *Endocrine Rev.* 4: 97–130). The results are summarized in Table 1 together with related sequence comparisons. Analysis of the proliferin amino acid sequence reveals that (1) mPLF and bPRL are more closely related than bPRL and bGH; (2) mPLF has significantly less homology to bPRL than do other mammalian prolactins, e.g., rat prolactin (rPRL); (3) the sequence of the first 29 amino acids of mPLF closely resembles the signal peptide of bPRL; (4) this mPLF leader sequence satifies the empirical rules for cleavage of a signal peptide after the serine residue at postion 29 (Von Heijne, 1983, *Eur. J. Biochem* 133: 17–21); (5) the sizes of the presumed precursor and mature mPLF polypeptides are very similar to those of bPRL; (6) the locations of the six cysteine and two tryptophan residues in mature bPRL and mPLF, diagrammed in FIG. 4, correspond almost precisely (these residues are highly conserved in the mammalian prolactins, see, Miller and Eberhardt, 1983, supra); (7) mPLF contains the sequences lys-lys-lys (positions 149-151 in the full length polypeptide) and lys-lys (174-175 and 205-206), which are often proteolytic cleavage sites in peptide hormones as well as three asn-x-ser regions (58-60, 75-77 and 88-90), the consensus signal for glycosylation. (Bahl in *The Glycoconjugates:* Vol. 1, pp. 385-422 (Horowitz & Pigmand eds. 1977).

TABLE I

RELATIONSHIP OF mPLF, mPRL[1], bPRL[1] and bGH[1]

| Proteins | Amino Acid Sequence Comparisons | | |
|---|---|---|---|
| | Identical | Related[2] | Total |
| mPLF × mPRL | 62 (32%) | 21 (11%) | 83 (43%) |
| mPLF × bPRL | 82 (37%) | 20 (9%) | 102 (46%) |
| mPLF × bGH | 50 (22%) | 23 (10%) | 73 (32%) |
| mPLF × bPRL or bGH | 99 (44%) | 20 (9%) | 119 (53%) |
| bPRL × bGH | 60 (26%) | 24 (10%) | 84 (37%) |
| bPRL × rPRL | 135 (59%) | 19 (8%) | 154 (68%) |

[1]Sequences taken from Miller and Eberhardt, 1983, Endocrine Rev. 4: 97–130; Kohomoto et al., 1984, Eur. J. Biochem. 138: 227–237.
[2]Related amino acids: lys and arg; asp and glu; asn and gln; ser and thr; val, leu and ile.

From the nucleotide sequence of proliferin cDNA one can infer that translation of the mRNA would yield a protein of about 25 kd containing 224 amino acid residues. A 25 kd protein is the major product of hybrid-selected proliferin mRNA translated in vitro. The amino acid sequence of proliferin shows a striking resemblance to that of bPRL and other mammalian prolactins. If closely related amino acids are included, mPLF and bPRL have 46% of their amino acid sequence in common, compared to 37% common sequences shared by gGH and bPRL; mPLF and mPRL have 43% of their amino acid sequences in common. Especially noteworthy are the nearly identical locations of the six cysteines, which form three disulfide bridges in prolactin (Niall in *Prolactin,* pp. 1–17, Jaffe ed., 1981), and the two tryptophans found in the body of proliferin and all prolactins sequenced so far, except for murine prolactin which has only one trypophan.

The predicted amino acid sequence of proliferin suggests that the protein may undergo a number of post-translational changes. There is an amino terminal hydrophobic region of 29 amino acids that resembles the signal peptide of prehormones, including prolactins; recently, evidence has been obtained that proliferin is secreted. The consensus glycosylation signal asn-x-ser appears at three locations in proliferin. Although this signal is not found in rat or bovine prolactin, ovine prolactin does have such a signal, and a glycosylated form of ovine prolactin has been reported (Lewis et al., 1984, *Proc. Natl. Acad. Sci. USA* 81: 385–389). Additionally, proliferin contains three regions with contiguous lysine residues, which could be sites for proteolytic cleavage (Steiner et al., 1980, *Annals NY Acad. Sci.* 343: 1–16; Docherty et al., 1982, *Ann. Rev. Physiol.* 44: 625–638).

Expression of Proliferin cDNA in Eucaryotes

Culture fluid from monkey cells infected with the mixed stock of SV40-PLF and SV40 helper virus contains glycosylated proliferin. Treatment of these cells with a drug that blocks glycosylation results in the secretion of non-glycosylated proliferin.

While the above specific embodiments are provided to illustrate the present invention, they are not intended to limit its scope because variations of the above embodiments are easily within the skill of the art.

We claim:

1. A DNA molecule containing a coding sequence free of introns for the amino acid sequence of mammalian proliferin.

2. A DNA molecule containing a coding sequence capable of being transcribed and translated in a procaryote into a protein containing the amino acid sequence of mammalian proliferin.

3. The DNA molecule of claim 1 wherein said molecule is contained within a procaryotic genome.

4. The DNA molecule of claim 3 wherein the coding sequence is associated with a procaryotic regulatory region enabling expression of said amino acid sequence.

5. The DNA molecule of claim 4 contained in a plasmid.

6. The DNA molecule of claim 1 contained in a procaryotic plasmid or bacteriophage vector.

7. The DNA molecule of claim 1 contained in a eucaryotic viral vector.

8. The DNA molecule of claim 7 wherein said viral vector is SV40 virus.

9. The DNA molecule of claim 1 wherein said molecule is contained in a eucaryotic genome.

10. The DNA molecule of claim 9 wherein said eukaryotic genome is contained within a eukaryotic cell and said cell expresses said amino acid sequence.

11. The DNA molecule of claim 10 wherein said amino acid sequence is expressed in a glycosylated form.

12. The DNA molecule of claim 1 containing a coding sequence for the amino acid sequence of proliferin said amino acid sequence being essentially as shown in FIG. 1.

13. The DNA molecule of claim 2 wherein the coding sequence is essentially as shown in FIG. 1.

14. The molecule of claim 1 contained in the plasmid PLF-1 deposited under ATCC Accession No. 39721.

15. A eucaryotic cell transformed by a DNA sequence containing a an intron-free coding sequence for mammalian proliferin and capable of expression as mature mammalian proliferin protein.

16. The cell of claim 15 wherein said DNA sequence is from the same species as said cell.

17. The cell of claim 15 wherein said transformed eucaryotic cell is from a cell line.

18. A cell line produced by clonally expanding the cell of claim 22 into a transformed cell line.

* * * * *